United States Patent [19]
Adams

[11] Patent Number: 5,803,509
[45] Date of Patent: Sep. 8, 1998

[54] LINE CONNECTOR LOCK

[76] Inventor: Robert D. Adams, 2 Meetinghouse Ct., Shamong, N.J. 08088

[21] Appl. No.: 847,698

[22] Filed: Apr. 28, 1997

[51] Int. Cl.$^6$ ..................................................... F16L 37/04
[52] U.S. Cl. ............................................ 285/114; 285/305
[58] Field of Search ................................... 285/114, 115, 285/117, 305

[56] References Cited

U.S. PATENT DOCUMENTS

| | | | |
|---|---|---|---|
| 4,230,109 | 10/1980 | Geiss | 285/114 |
| 4,307,903 | 12/1981 | Wallace | 285/114 |
| 4,340,244 | 7/1982 | Scott | 285/114 |
| 4,641,646 | 2/1987 | Schultz et al. | 285/114 |
| 4,846,167 | 7/1989 | Tibbals | 285/114 |
| 5,248,306 | 9/1993 | Clark et al. | 285/114 |

FOREIGN PATENT DOCUMENTS

| | | | |
|---|---|---|---|
| 4241385 | 6/1993 | Germany | 285/114 |
| 4-107386 | 4/1992 | Japan | 285/114 |
| 432223 | 7/1935 | United Kingdom | 285/114 |
| 1007746 | 10/1965 | United Kingdom | 285/114 |
| 2205137 | 11/1988 | United Kingdom | 285/114 |
| 2274887 | 8/1994 | United Kingdom | 285/114 |

*Primary Examiner*—Eric K. Nicholson
*Attorney, Agent, or Firm*—Volpe and Koenig, P.C.

[57] ABSTRACT

A line connector lock is used with intravenous (IV) or feeding tube connections to prevent inadvertent disconnections or fluid contamination. The line connector lock has a hollow body and a tensioning element attached to the body. The body fits over an insertion tube and is forced against a line connection through the tensioning element. Installation and removal of the line connector lock is possible on existing tube connections. The two ends of the line connector lock are preferably of different diameters to accommodate various types and sizes of connections.

17 Claims, 5 Drawing Sheets

this invention relates to…

LINE CONNECTOR LOCK

BACKGROUND OF THE INVENTION

1. Field of the Invention

This invention relates to a device for securing a tubular connection. More particularly, it concerns the securing a tubular connection of an intravenous (IV) tube or feeding tube system. When used, the line connector lock ensures the continued in-line connection between two tubes, stopping inadvertent disconnection failures and/or fluid contamination.

2. Description of the Prior Art

Prior Art techniques for securing an intravenous tube or feeding tube still basically consists of taping and tieing techniques. Although some particular devices have been proposed for this purpose, the known Prior Art devices generally rely upon some connection to the patient.

SUMMARY OF THE INVENTION

The present invention provides a locking mechanism for detachable tubular connections. The locking mechanism overcomes the problem of leakage and unintentional disconnection of the tubular connection. Additionally, the present invention permits locking of tubular connections for both screw-type and linear-type connections. The present locking device permits installation on and removal from existing tubular connections.

DESCRIPTION OF THE PREFERRED EMBODIMENTS

Figure 1:
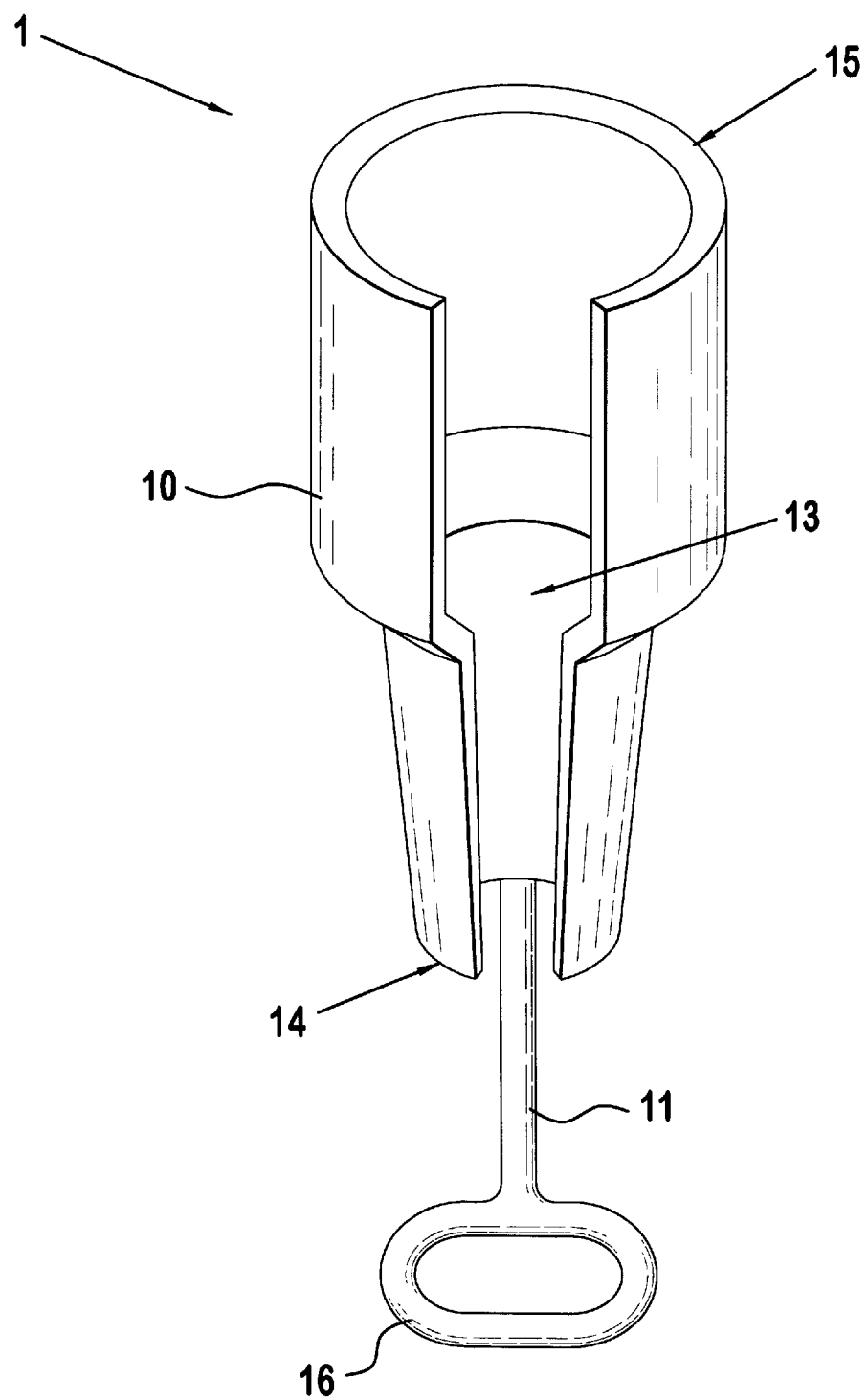
FIG. 1 is a front elevation of the invention.

As shown in FIG. 1, a front elevation, line connector lock 1 has a cylinder body 10, a longitudinal slot or opening 13, and a tensioning element 11. One end of the tensioning element 11 is connected to the body 10 at an attachment point (not shown) with the other end of the tensioning element 11 forming a loop 16. The body 10 is preferably made of resilient material. The longitudinal slot 13 extends between ends 14 and 15 of the body 10. Ends 14 and 15 have different circumferences which extend to about the midportion of the body 10 where they meet. This allows for a size selection between the two ends when engaging the line connector lock 1 on a tubular connection.

Figure 2:
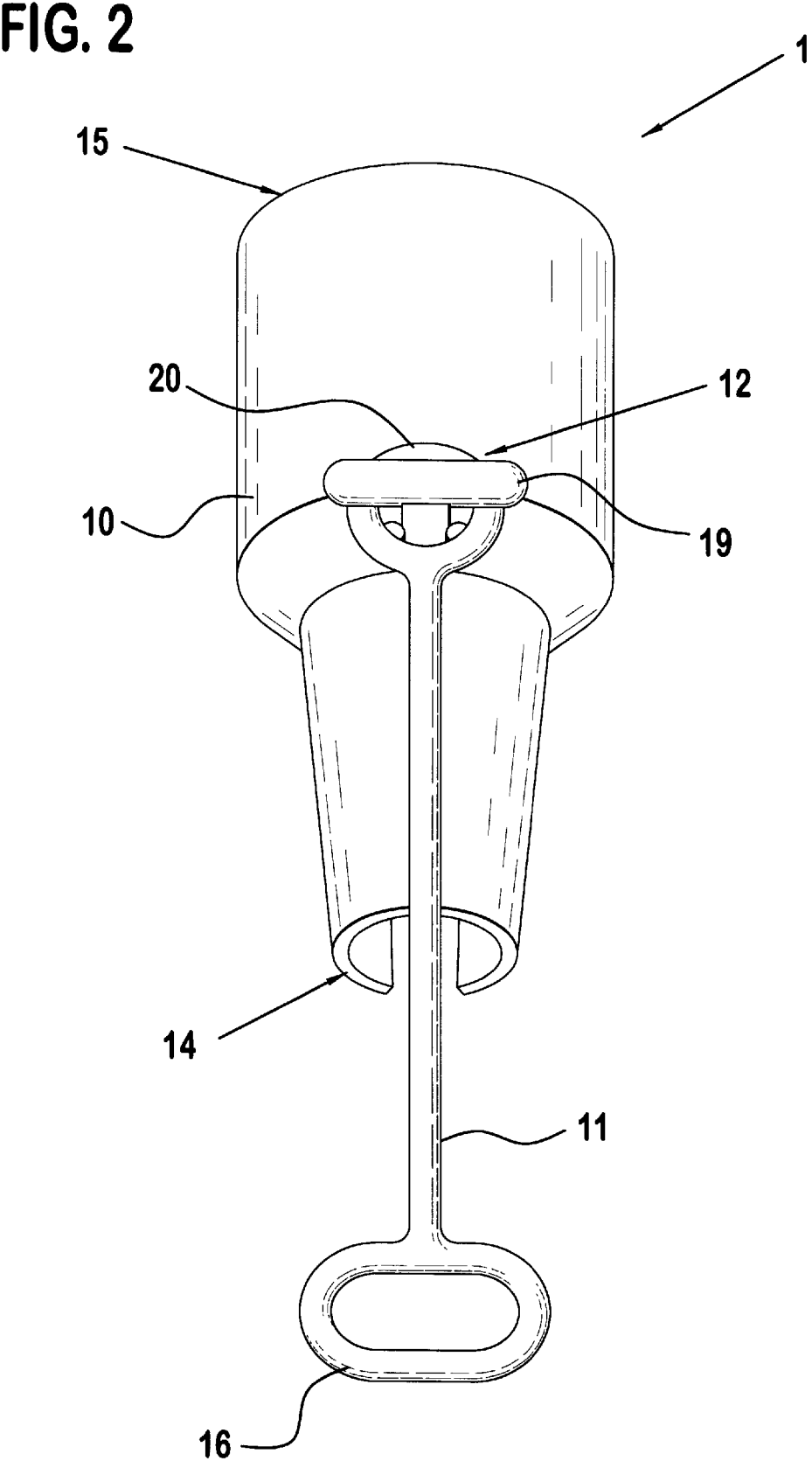
FIG. 2 is a rear elevation of the invention.

FIG. 2 shows a rear elevation of the line connector lock 1. Tensioning element 11 is attached to body 10 at attachment point 12. Loop 20 of tensioning element 11 is placed around a "T" shaped projection 19 which is part of the body 10. The attachment point 12 allows rotational movement of the tensioning element 11 in relation to the body 10. Alternatively, tensioning element 11 may be attached to the body 10 by being directly molded thereto. Tensioning element 11 is preferably an elastic material, which allows elastic deformation at least along the length thereof. In the currently preferred embodiment, loops 16 and 20 are also elastic and the body 10 is of a moldable plastic material.

Figure 3:
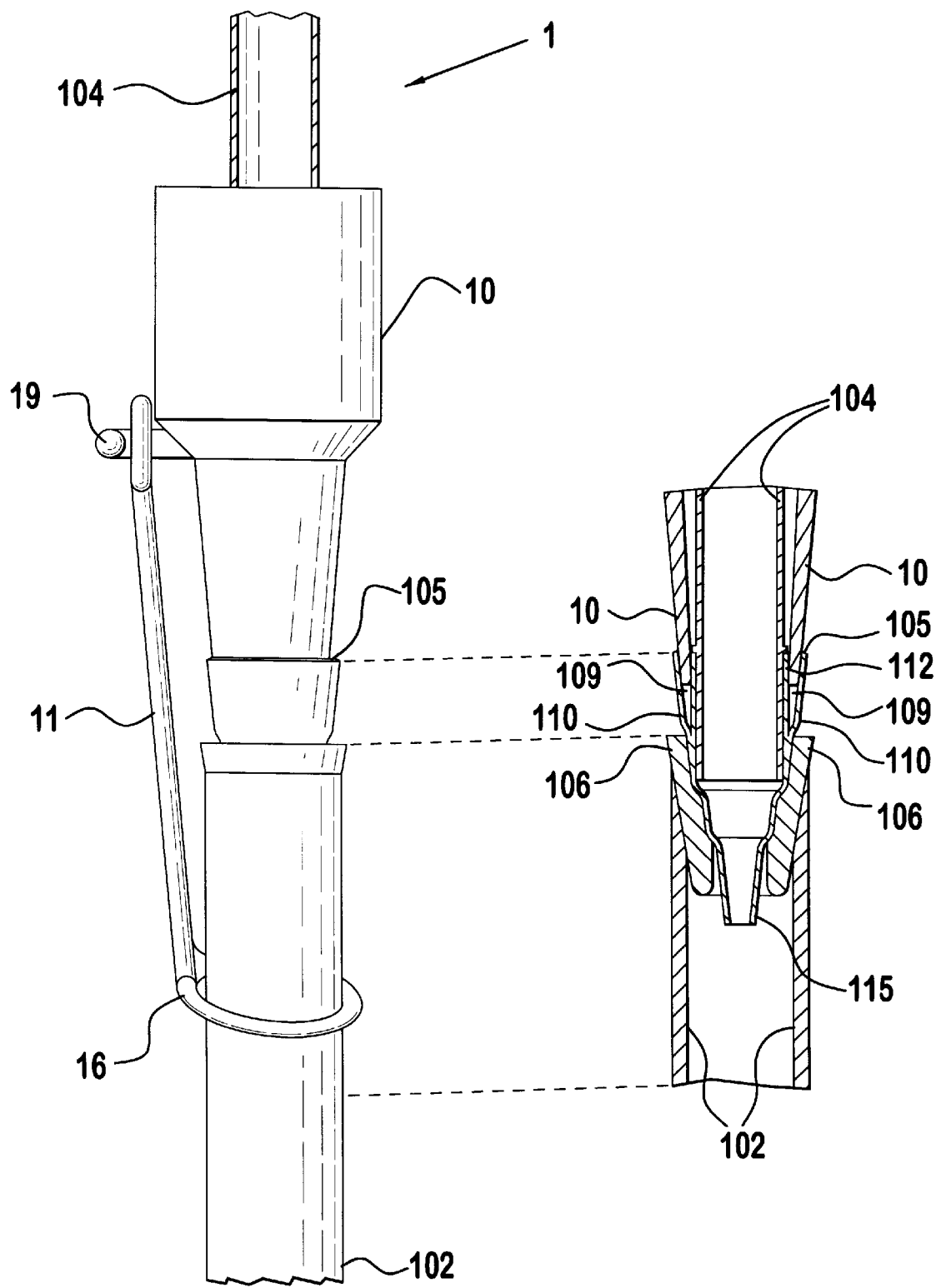
FIG. 3 illustrates the invention in use on a tubular connection.

In FIG. 3, the line connector lock 1 is shown on a line connection formed between male portion 115 attached to an insertion tube 104 and female portion 106 attached to a receiving tube 102. The male portion 115 has first circumferential ring 112 and second circumferential ring 110 which define a recess or cavity 109 therebetween. Recess 109 and edge 105 of circumferential ring 110 remain exposed after the male portion 115 is inserted into the female portion 106.

To use line connector lock 1, loop 16 is placed around receiving tube 102 prior to mating the male portion 115 with the female portion 106 and body 10 is positioned to end 14 can be inserted into recess 109. As noted previously, the body 10 is rotatable about attachment point 12, and tensioning element 11 is elastically extendable. Longitudinal slot 13 allows the body 10 to be inserted over tube 104. Once inserted in cavity 109, end 14 is urged against the inter walls defining recess 109. Loop 16 remains in frictionally engagement with tube 102 to maintain a force on body 10, and retain the connection between portions 106 and 115.

Figure 4:
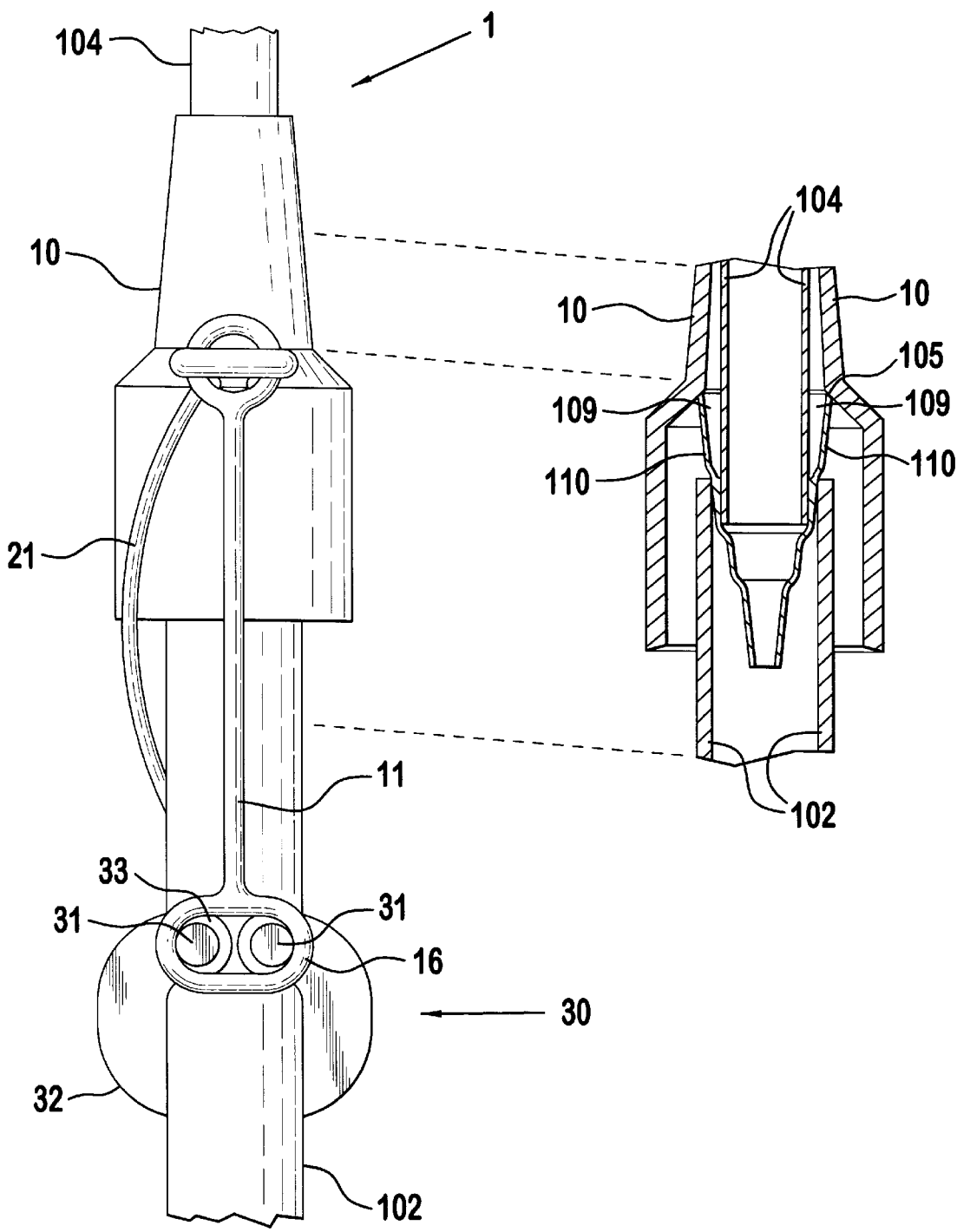
FIG. 4 illustrates the alternative embodiment of the invention in use on a tubular connection.

The attachment point 12 allows rotation of the body 10 to place either small end 14 or large end 15 against the male portion 115. Small end 14 inserts into the cavity area 109, as shown in FIG. 3, and ensures positive and secure placement of the body 10 in relation to the male portion 115. The large end 15 of body 10 permits capping over the edge 105 of the male portion 115, as shown in FIG. 4, should this be necessary. When using large end 15, it is unnecessary for the male portion 115 to form a cavity area. The large end 15 lays over the edge 105 of the male portion 115, and the locking force is imparted onto the male portion 115 from the body 10 through the edge 105 to the male portion 115. This versatility between ends 14 and 15 of the body 10 allows for varying configurations of line connections and multiple uses of the line connector lock 1.

Figure 5:
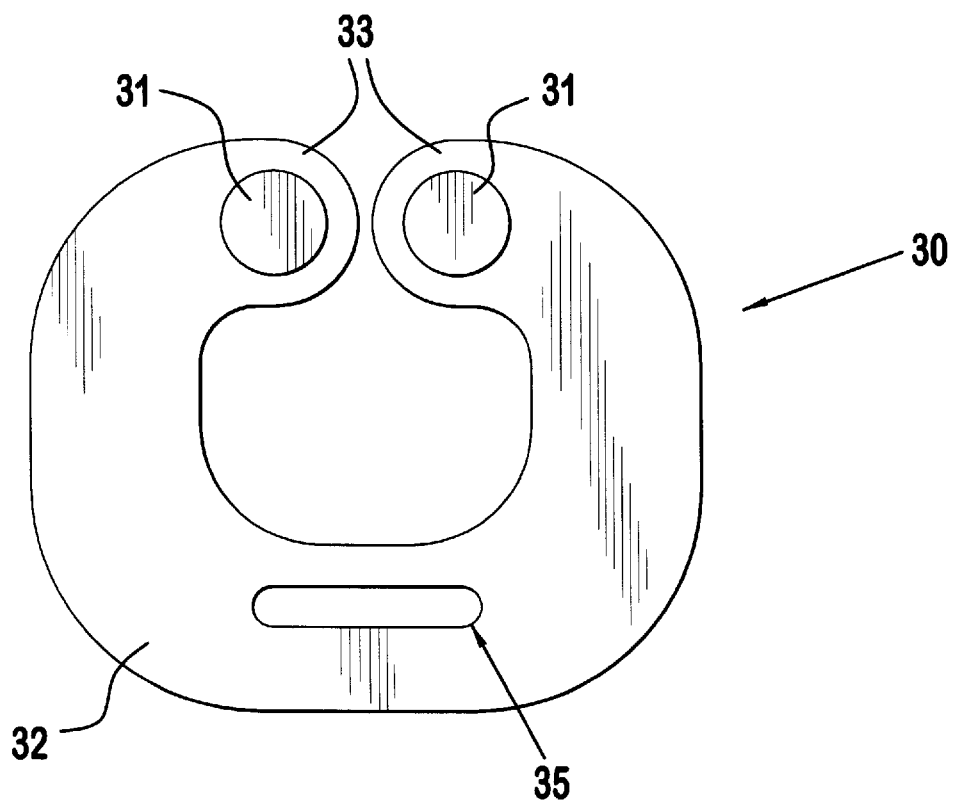
FIG. 5 is a tie anchor for use with the alternative embodiment of the invention.

An alternative embodiment, illustrated in FIGS. 4 and 5, shows the line connector lock 1 on a line connection formed between the male portion 115 on the insertion tube 104 directly mated into the receiving tube 102. Loop 16 of tensioning element 11 remains engaged and attached to a raised surface 31 of a tie anchor 30, which is independently shown in FIG. 5. The tie anchor 30 has a base portion 32, wings 33 and raised surfaces 31 on the same side of the wings 33. Wings 33 are configured to receive a tube therebetween into an area formed by wings 33 and base portion 32. The tie anchor 30 allows installment and removal of the line connector lock 1 without the need to disconnect a line connection.

Installation of the tie anchor 30 is performed by inserting the receiving tube 102 between the wings 33. Afterward, loop 16 is placed around raised surfaces 31 to force the wings 33 close together so they firmly hold against the receiving tube 102 through frictional force. This holds the tie anchor 30 in place along the receiving tube 102 while the elastic tensioning element 11 remains elongated. The body 10 is manually extended beyond the edge 105 to a position along side of the insertion tube 104 by elastically extending the tensioning element 11. The body 10 is rotated about attachment point 12 to permit large end 15 to be placed in the direction of the edge 105. The insertion tube 104 is placed through the longitudinal slot 13 and encapsulated by the body 10. The body 10 traverses along the insertion tube 104 towards the edge 105 and large end 15 is capped over the edge 105, forcing the inter wall of body 10 against the edge 105. After the inter wall of body 10 is placed against the edge 105, the elongated condition of tensioning element 11 continuously forces the body 10 against the edge 105 of the male portion 115, thereby forcing and locking the insertion tube 104 into the receiving tube 102. The amount of force of the body 10 against the edge 105 is proportional to the distance of the tie anchor 30 from the edge 105. Removing the tie anchor 30 requires that the loop 16 is unfastened from the raised surfaces 31, thereafter the receiving tube 102 is manually pushed between the wings 33 away from the base portion 32, disengaging the tie anchor 30 from the receiving tube 102. The tie anchor 30 may also have a hole or fastening device 35 which allows it to remain connected to the body 10, through a tether 21, when the line connector lock 1 is not in use.

I claim:

1. A security device for a connection that joins the ends of tubular conductors, the device comprising:

a slotted hollow body having first and second ends and an attachment point for attaching an elastic element to the body; and an elastic element having a first portion configured to mate with the attachment point and another portion configured for attachment at a position at a distance from the attachment point, the elastic element having a predetermined length in a relaxed state that is less than the distance between the point and the position so that the elastic element is under tension when both portions are attached.

2. The device of claim 1 wherein the first end and second end of the body are of different diameters.

3. The device of claim 2 wherein the body has a generally conical shape.

4. The device of claim 1 wherein the attachment point is located between the first and second ends.

5. The device of claim 1 wherein the elastic element portion mated with the attachment point forms an end of the elastic element.

6. The device of claim 1 wherein the elastic element is rotatably attached to the body at the attachment point.

7. The device of claim 1 wherein at least one body end is configured for inserting into a cavity area.

8. The device of claim 1 wherein at least one body end is configured for capping over a Luer lock of an IV connector.

9. The device of claim 1 wherein the elastic element is molded to the body at the attachment point.

10. The device of claim 1 wherein the tensioning element is detachably attached to the body at the attachment point.

11. The device of claim 1 wherein the body is made of a resilient material.

12. The device of claim 1 wherein at least one body end has a larger diameter than a middle portion of the body.

13. The device of claim 1 wherein the elastic element has a tie anchor.

14. The device of claim 13 wherein the elastic element further comprises a tether attached between the tie anchor and the body.

15. The device of claim 1 wherein the elastic element forms a loop on at least one end thereof.

16. The device of claim 13 wherein the tie anchor is detachable.

17. The device of claim 1 wherein the body has a generally tubular shape.

* * * * *